(12) United States Patent
Abe et al.

(10) Patent No.: US 7,726,879 B2
(45) Date of Patent: Jun. 1, 2010

(54) X-RAY IMAGING APPARATUS, CONTROL METHOD FOR X-RAY IMAGING APPARATUS, PROGRAM, AND STORAGE MEDIUM

(75) Inventors: Masahiro Abe, Yamato (JP); Tsukasa Sako, Yokohama (JP); Yuichi Nishii, Tokyo (JP); Hideto Shiozawa, Shuwa (JP)

(73) Assignee: Canon Kabushiki Kaisha, Tokyo (JP)

( * ) Notice: Subject to any disclaimer, the term of this patent is extended or adjusted under 35 U.S.C. 154(b) by 101 days.

(21) Appl. No.: 12/247,592

(22) Filed: Oct. 8, 2008

(65) Prior Publication Data

US 2009/0103678 A1    Apr. 23, 2009

(30) Foreign Application Priority Data

Oct. 23, 2007 (JP) .............................. 2007-275670

(51) Int. Cl.
*G01N 23/04* (2006.01)

(52) U.S. Cl. ...................................... 378/206; 378/94

(58) Field of Classification Search ......... 378/205–206, 378/94, 98
See application file for complete search history.

(56) References Cited

U.S. PATENT DOCUMENTS

| 6,473,489 B2 * | 10/2002 | Bani-Hashemi et al. ....... 378/63 |
| 7,344,305 B2 * | 3/2008 | Kuzmanovic ............... 378/206 |
| 2003/0223540 A1 * | 12/2003 | Hayashida et al. ......... 378/98.8 |

FOREIGN PATENT DOCUMENTS

JP          54-158984          12/1979

\* cited by examiner

*Primary Examiner*—Hoon Song
(74) *Attorney, Agent, or Firm*—Cowan, Liebowitz & Latman, P.C.

(57) ABSTRACT

An X-ray imaging apparatus includes a visible light imaging unit which captures an image of a visual field region with visible light, an X-ray irradiation unit which irradiates X-rays, an X-ray imaging unit which receives the irradiated X-rays and acquires a radiograph based on the X-rays, and a detection unit which detects an irradiated region irradiated with the X-rays based on the acquired radiograph.

14 Claims, 6 Drawing Sheets

X-RAY IMAGING APPARATUS, CONTROL METHOD FOR X-RAY IMAGING APPARATUS, PROGRAM, AND STORAGE MEDIUM

BACKGROUND OF THE INVENTION

1. Field of the Invention

The present invention relates to an X-ray imaging technique.

2. Description of the Related Art

Conventionally, an X-ray imaging apparatus used in a hospital or the like uses a cassette. After an exposed cassette is developed, the developed film is interpreted by using an observation device called a film viewer. With the recent advances in digitization, image data are directly displayed as images on a monitor and observed without development of a film. These operations are performed to make examination and to observe the inner state of the body, for example, whether there is a tumor or the state of bone fracture.

In addition, recent X-ray imaging apparatuses have begun to be used as surgical auxiliary apparatuses instead of apparatuses for examination. For example, in executing cardiac catheterization, an operator generally performs treatment by tracking a catheter inserted into the body while observing radioscopic pictures. In this case, it is thought that puncturing operation can be effectively performed by capturing images by an X-ray imaging apparatus and superimposing/displaying visible images and radiographs as guide information for puncturing on a TV monitor so as to allow the operator to grasp a specific portion at which puncturing should be started. For example, Japanese Patent Laid-Open No. 54-158984 discloses an arrangement configured to superimpose and display radioscopic pictures and visible images on a monitor.

The technique disclosed in Japanese Patent Laid-Open No. 54-158984, however, is aimed at the examination of semiconductor wafers, and hence gives no consideration to changes in the relative positional relationship between an X-ray tube and an X-ray detection unit. Consider, for example, a nursing apparatus using an X-ray sensor (X-ray detection unit) called a cassette which can be arbitrarily placed. In this case, when the relative positions of the X-ray tube and X-ray sensor are changed, it is impossible to detect a positional shift. For this reason, the X-ray imaging apparatus cannot inform the user of the occurrence of the positional shift. As a consequence, the user must recognize the occurrence of the positional shift upon occurrence of an error in a capturing result, and position the X-ray sensor and the X-ray tube again.

SUMMARY OF THE INVENTION

The present invention has been made in consideration of the above problems, and has as its object to provide an X-ray imaging technique which can control X-ray irradiation, during movie shooting by X-ray imaging of an object, on the basis of the detection result obtained by detecting the presence/absence of a relative positional shift between an X-ray irradiation unit and an X-ray imaging unit.

According to one aspect of the present invention, there is provided an X-ray imaging apparatus comprising:

a visible light imaging unit adapted to capture an image of a visual field region with visible light;

an X-ray irradiation unit adapted to irradiate X-rays;

an X-ray imaging unit adapted to receive X-rays irradiated by the X-ray irradiation unit and acquire a radiograph based on the X-rays;

a detection unit adapted to detect a region irradiated with the X-rays on the basis of a radiograph acquired by the X-ray imaging unit;

a registration unit adapted to register position information of the irradiated region of an image of the visual field region in a still image shooting mode;

a detection unit adapted to detect the presence/absence of a relative positional shift between the X-ray irradiation unit and the X-ray imaging unit by comparing position information registered by the registration unit with position information based on an irradiated region of a radiograph acquired during movie shooting of performing X-ray imaging of an object; and an irradiation control unit adapted to control irradiation of the X-rays by the X-ray irradiation unit based on a detection result obtained by the positional shift detection unit.

According to another aspect of the present invention, there is provided a control method for an X-ray imaging apparatus, the method comprising:

a visible light capturing step of causing a visible light imaging unit to capture an image of a visual field region with visible light;

an X-ray irradiation step of causing an X-ray irradiation unit to irradiate X-rays;

an x-ray image capturing step of causing an X-ray imaging unit to receive X-rays irradiated in the X-ray irradiation step and acquire a radiograph based on the X-rays;

a detection step of causing a detection unit to detect an irradiated region irradiated with the X-rays based on a radiograph acquired in the X-ray image capturing step;

a registration step of causing a registration unit to register position information of the irradiated region of an image of the visual field region in a still image shooting mode;

a positional shift detection step of causing a positional shift detection unit to detect the presence/absence of a relative positional shift between the X-ray irradiation unit and the X-ray imaging unit by comparing position information registered in the registration step with position information based on an irradiated region of a radiograph acquired during movie shooting of performing X-ray imaging of an object; and an irradiation control step of causing an irradiation control unit to control irradiation of the X-rays in the step of irradiating X-rays on the basis of a detection result obtained in the positional shift detection step.

According to the present invention, it is possible to control X-ray irradiation, during movie shooing by X-ray imaging of an object, based on the detection result obtained by detecting the presence/absence of a relative positional shift between an X-ray irradiation unit and an X-ray imaging unit.

Alternatively, when it is determined based on a detection result indicating the presence/absence of a positional shift that a positional shift has occurred, it is possible to prevent excessive irradiation or leakage of X-rays by performing control to stop X-ray irradiation.

Alternatively, displaying guide information for guiding the user in operation to correct the relative positional shift between the X-ray irradiation unit and the X-ray imaging unit can implement an X-ray imaging apparatus with high convenience.

Further features of the present invention will become apparent from the following description of exemplary embodiments with reference to the attached drawings.

DESCRIPTION OF THE EMBODIMENTS

The preferred embodiments of the present invention will be described exemplarily in detail below with reference to the accompanying drawings. The constituent elements described in these embodiments are merely examples. The technical range of the present invention is defined by claims, but is not limited by each embodiment to be described below.

First Embodiment

Figure 1:
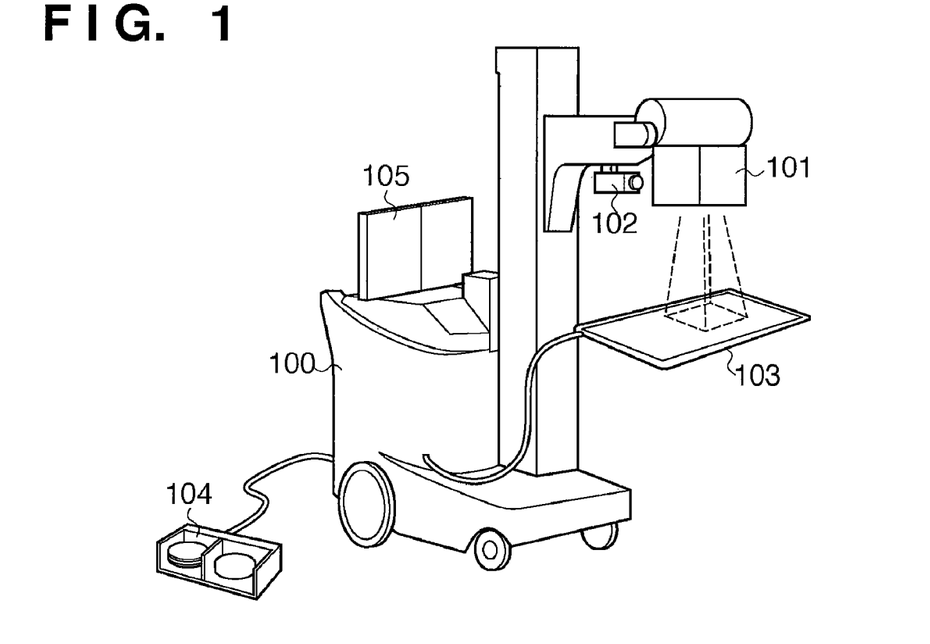
FIG. 1 is a perspective view exemplarily showing the outer appearance of an X-ray imaging apparatus according to an embodiment of the present invention.

FIG. 1 is a view exemplarily showing the outer appearance of an X-ray imaging apparatus according to the first embodiment of the present invention. The X-ray imaging apparatus can be moved by a nursing cart 100 including a moving mechanism, and comprises an X-ray generation unit 101, a TV camera 102, an X-ray sensor 103, a foot pedal 104, and a display unit 105. The housing of the nursing cart 100 incorporates a control apparatus for controlling the X-ray imaging apparatus. The control apparatus can control X-ray irradiation by the X-ray generation unit 101 on the basis of radiograph signals acquired by the X-ray sensor 103, operation inputs from the foot pedal 104, and the like.

The X-ray generation unit 101 includes a mechanism for generating X-rays, which comprises an X-ray tube, an X-ray collimator, and the like. The TV camera 102 is placed at a conjugate position to the X-ray tube via a half mirror provided in the X-ray generation unit 101, and can capture a target irradiated with X-rays. The TV camera 102 and the X-ray generation unit 101 will be described in detail later. The X-ray sensor 103 is a sensor which receives X-rays irradiated by the X-ray generation unit 101, and acquires an image signal. The image signal acquired by the X-ray sensor is input to the control apparatus.

The foot pedal 104 is an input device for instructing the control apparatus to irradiate X-rays or stop irradiation. The control apparatus can control irradiation of X-rays and the stoppage of X-ray irradiation by controlling the X-ray generation unit 101 based on inputs from the foot pedal 104. The display unit 105 comprises a general monitor such as a CRT or liquid crystal display, and displays image data, a GUI (Graphical User Interface), and the like on the screen. The control apparatus can execute display control to display an X-ray imaging result as image data on the display unit 105.

Note that the X-ray imaging apparatus comprises general input devices such as a keyboard and mouse (not shown) in addition to the foot pedal 104. The user can input instructions to the control apparatus via the input devices such as the keyboard and mouse so as to operate and control the X-ray imaging apparatus.

Figure 2:
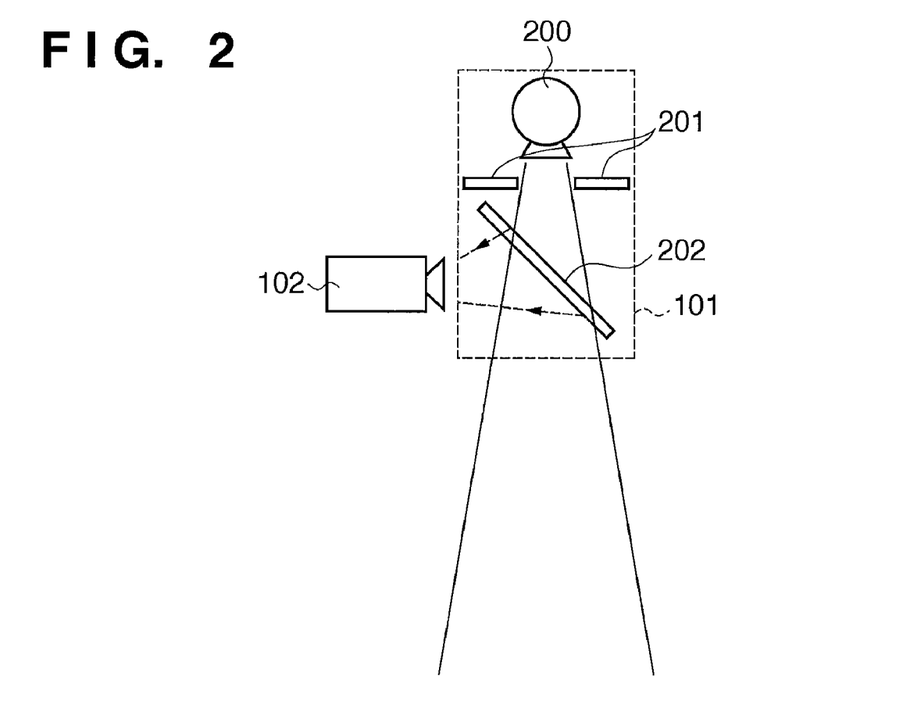
FIG. 2 is a view schematically showing the arrangement of an X-ray generation unit and the positional relationship between the X-ray generation unit and a TV camera.

The positional relationship between the X-ray generation unit 101 and the TV camera 102 will be described next. FIG. 2 is a view for schematically explaining the arrangement of the X-ray generation unit 101 and the positional relationship between the X-ray generation unit 101 and the TV camera 102. FIG. 2 also shows the arrangement of the X-ray generation unit 101.

The X-ray generation unit 101 comprises an X-ray tube 200 which generates X-rays, a collimator 201 for limiting the irradiation direction and irradiated region of X-rays generated by the X-ray tube 200, and a half mirror 202 which transmits X-rays and reflects visible light. The TV camera 102 is placed at a position optically equivalent (conjugate) to that of the X-ray tube 200. Note that the TV camera 102 is preferably placed at a position where it can capture the image reflected by the half mirror 202 which is placed outside the collimator 201 so as to prevent the collimator 201 from focusing visible light.

Figure 3:
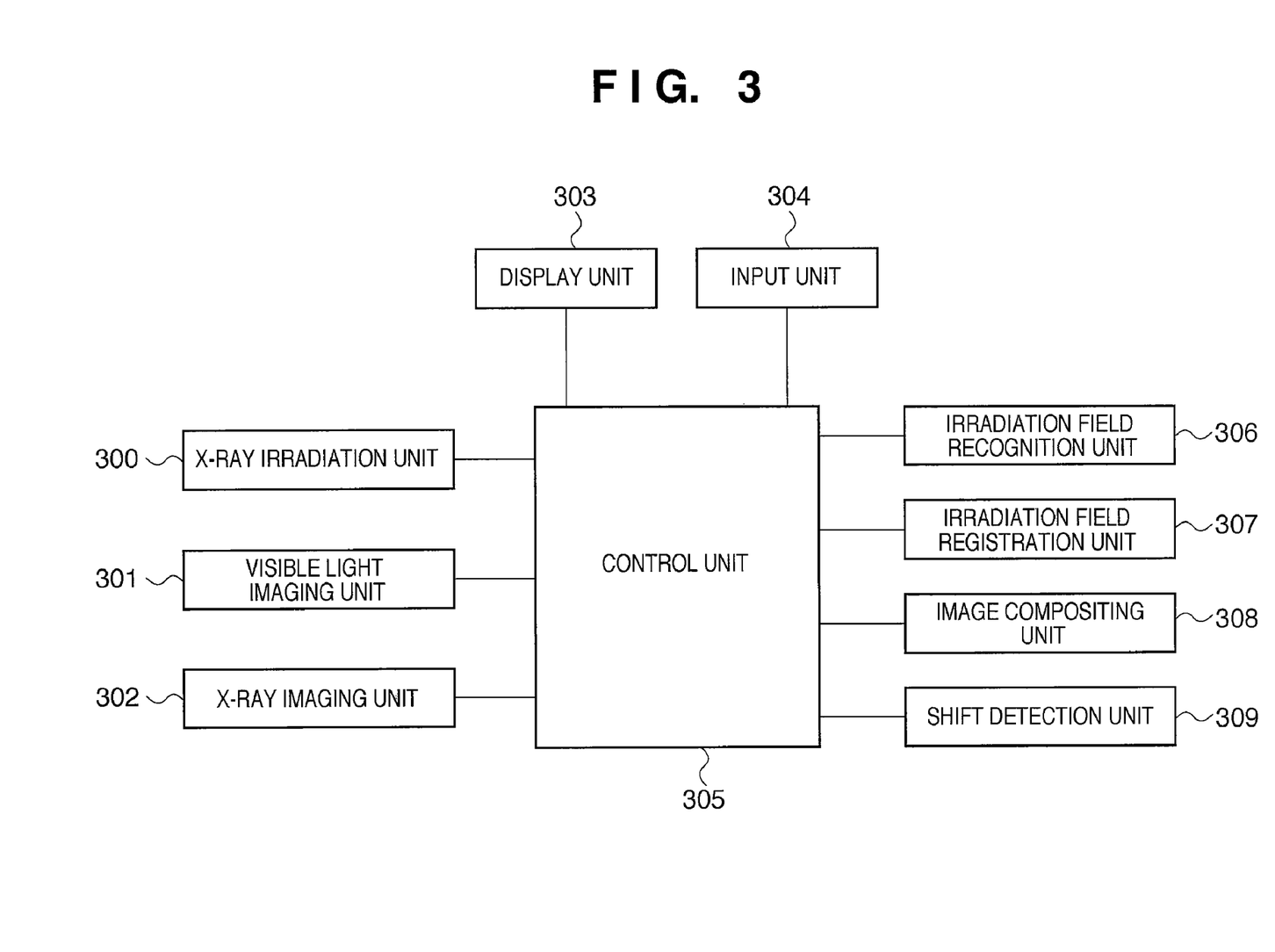
FIG. 3 is a block diagram showing the functional arrangement of the X-ray imaging apparatus according to the embodiment of the present invention.

The functional arrangement of the X-ray imaging apparatus will be described next. FIG. 3 is a block diagram showing the functional arrangement of the X-ray imaging apparatus according to the first embodiment of the present invention.

An X-ray irradiation unit 300 corresponds to the functional arrangement of the X-ray generation unit 101 in FIG. 1. The X-ray irradiation unit 300 can generate X-rays and irradiate the X-rays to an object. A visible light imaging unit 301 corresponds to the functional arrangement of the TV camera 102, and can capture an object image reflected by the half mirror 202.

An X-ray imaging unit 302 corresponds to the functional arrangement of the X-ray sensor 103, and can acquire a radiograph (X-ray signal) based on received X-rays.

A control unit 305 receives an imaging start (irradiation start) instruction addressed to the X-ray irradiation unit 300 and image data from the X-ray imaging unit 302, and can perform overall control on the X-ray imaging apparatus. In this case, the control unit 305 functions as an irradiation control means for controlling X-ray irradiation. The control unit 305 implements the functional arrangement of the control apparatus housed in the housing of the nursing cart 100. The control unit 305 includes a CPU (not shown) for executing control on the X-ray imaging apparatus, a memory (not shown) such as a ROM which stores programs executed by the CPU, and a memory (not shown) such as a RAM functioning as a work area of the CPU.

An irradiation field recognition unit 306 is a recognition unit which recognizes the irradiated region (irradiation field) of X-rays irradiated to the X-ray sensor 103. The irradiation field recognition unit 306 has a function of discriminating a portion irradiated with X-rays and a portion irradiated with no X-rays on the surface of the X-ray sensor 103 by image processing.

An irradiation field registration unit 307 registers the irradiated region detected by the irradiation field recognition unit 306 with respect to the picture captured by the visible light imaging unit 301. An image compositing unit 308 composites the visible image and the radiograph obtained by the visible light imaging unit 301 and the X-ray imaging unit 302. The image compositing unit 308 can generate a composite image by changing the transparency of either or both of the radiograph and the visible image and compositing them such that the radiograph is seen through the visible image.

A shift detection unit 309 measures the overlap state of the visible image and the radiograph based on the position information (irradiation field information) of the irradiated region registered by the irradiation field registration unit 307, and detects the shift between them.

Information processing performed by the cooperation between the programs stored in the ROM and the like of the control unit 305 and the CPU implements the above functions of the control unit 305, irradiation field recognition unit 306, irradiation field registration unit 307, image compositing unit 308, and shift detection unit 309.

The programs to be used are not limited to those stored in the ROM and the like. For example, a hard disk (not shown) in which programs are installed can be further provided, and each program can be downloaded from the hard disk at the time of execution.

A display unit 303 corresponds to the functional arrangement of the display unit 105 in FIG. 1. The display unit 303 can control the display of the display unit 105 on the basis of the information received from the control unit 305. An input unit 304 corresponds to the functional arrangements of general input devices such as a mouse and keyboard, in addition to the foot pedal 104 in FIG. 1, with which the user issues various operation instructions to the X-ray imaging apparatus.

(Processing Sequence at Time of X-Ray Imaging)

A processing sequence at the time of X-ray imaging in the X-ray imaging apparatus according to this embodiment will be described next with reference to the flowchart of FIG. 4.

First of all, in step S401, the visible light imaging unit 301 starts capturing an image of a visual field region with visible light. That is, the TV camera 102 starts capturing a visible image of an object which is reflected by the half mirror 202. This imaging processing is continued while X-ray radioscopy is performed subsequently.

In step S402, the control unit 305 executes X-ray still image shooting in the still image shooting mode by causing the X-ray generation unit 101 to irradiate X-rays. When the user performs input operation, for example, stepping on the foot pedal 104, an instruction to start X-ray irradiation is input to the control unit 305. Upon receiving the X-ray irradiation start instruction, the control unit 305 controls the X-ray generation unit 101. The X-ray generation unit 101 then starts irradiating X-rays. The X-ray sensor 103 receives the X-rays irradiated from the X-ray generation unit 101. The X-ray sensor 103 then transmits image data (X-ray still image) as a result of X-ray imaging to the control unit 305. This step is preferably performed before the object is placed, in order to prevent the object from being exposed to X-rays.

In step S403, the irradiation field recognition unit 306 detects an irradiated region actually irradiated with X-rays based on the radiograph captured in step S402.

In step S404, the irradiation field registration unit 307 registers the irradiated region (irradiation field) of X-rays detected in step S403 with respect to an image (visible image) of a visual filed which is captured in step S401. In the still image shooting mode, the irradiation field registration unit 307 registers position information indicating that a specific portion of the visible image is an X-ray imaging region. This position information is registered in a memory such as the RAM (not shown) of the control unit 305.

In step S405, X-ray radioscopic imaging is started under the control of the control unit 305. X-ray radioscopic imaging is so-called X-ray movie shooting operation of performing X-ray imaging by continuously generating X-rays. X-ray radioscopic imaging is executed on the basis of operation inputs to the control unit 305 while, for example, the user keeps stepping on the foot pedal 104. The X-ray sensor 103 receives the X-rays irradiated from the X-ray generation unit 101, and sequentially transmits image data obtained as a result of X-ray imaging to the control unit 305.

In step S406, the irradiation field recognition unit 306 discriminates the irradiated region (irradiation field) irradiated with X-rays on the light-receiving surface of the X-ray sensor 103 during X-ray radioscopic imaging.

In step S407, the image compositing unit 308 superimposes the radiograph captured as a moving image and a visible image. At this time, the image compositing unit 308 can also generate a composite image by changing the transparency of either or both of the radiograph and the visible image and combining them such that the radiograph is seen through the visible image.

In step S408, the shift detection unit 309 detects the presence/absence of a relative positional shift between the X-ray irradiation unit and the X-ray imaging unit by comparing the registered position information with the position information based on the irradiated region of the radiograph acquired during movie shooting.

It is possible to detect the presence/absence of a relative positional shift between the X-ray tube 200 and the X-ray sensor 103 by registering in advance information indicating which part of a visible image corresponds to an X-ray irradiation field region and comparing the information with the position information registered during X-ray radioscopy.

If it is determined, based on the detection result in step S408 described above, in step S409 that there is a positional shift (YES in step S409), the process advances to step S411. If it is determined that there is no positional shift (NO in step S409), the process advances to step S410.

In step S410, the composite image generated in step S407 is displayed on the display unit 105 under the display control of the control unit 305.

In step S411, the control unit 305 receives, from the shift detection unit 309, the determination result indicating the presence of a positional shift during movie shooting. The control unit 305 stops irradiation of X-rays based on the determination result indicating the presence of the positional shift, and transmits an imaging stop signal to the X-ray generation unit 101 to stop movie shooting. The X-ray generation unit 101 stops irradiation of X-rays on the basis of the reception of the imaging stop signal.

In step S412, the control unit 305 calculates a positional shift amount based on the detection result obtained by the shift detection unit 309 after stopping radioscopic imaging with X-ray irradiation. In order to correct the positional shift amount based on the calculation result on the positional shift amount, the image compositing unit 308 can display guide information for guiding the user to position the X-ray generation unit 101 or the X-ray sensor 103 in the composite image generated in step S407. For example, the image compositing unit 308 displays, on the display unit 105, guide information indicating how to move either or both of the X-ray sensor 103 and the X-ray tube in order to restore the initial state without any positional shift. By referring to the guide information, for example, the user can correct the relative positional shift between the X-ray sensor 103 and the X-ray generation unit 101. After the positional shift is corrected, the process returns to step S401 to allow repetitive execution of the same processing.

Note that providing a moving mechanism for moving the X-ray sensor 103 and the X-ray generation unit 101 makes it possible to correct the positional shift between the X-ray sensor 103 and the X-ray generation unit 101 by controlling the moving mechanism under the control of the control unit 305.

(Registration of Irradiation Field and Detection of Positional Shift)

Registration of an irradiated region and detection processing for a positional shift will be described next with reference to FIGS. 5A and 5B. Reference numeral 51a in FIG. 5A denotes a view showing the positional relationship between the X-ray tube 200, the X-ray sensor 103, and an object 500. Reference numeral 52b in FIG. 5A denotes a view schematically showing the relationship between images obtained owing to the positional relationship in the view 51a in FIG. 5A.

Figure 5A:
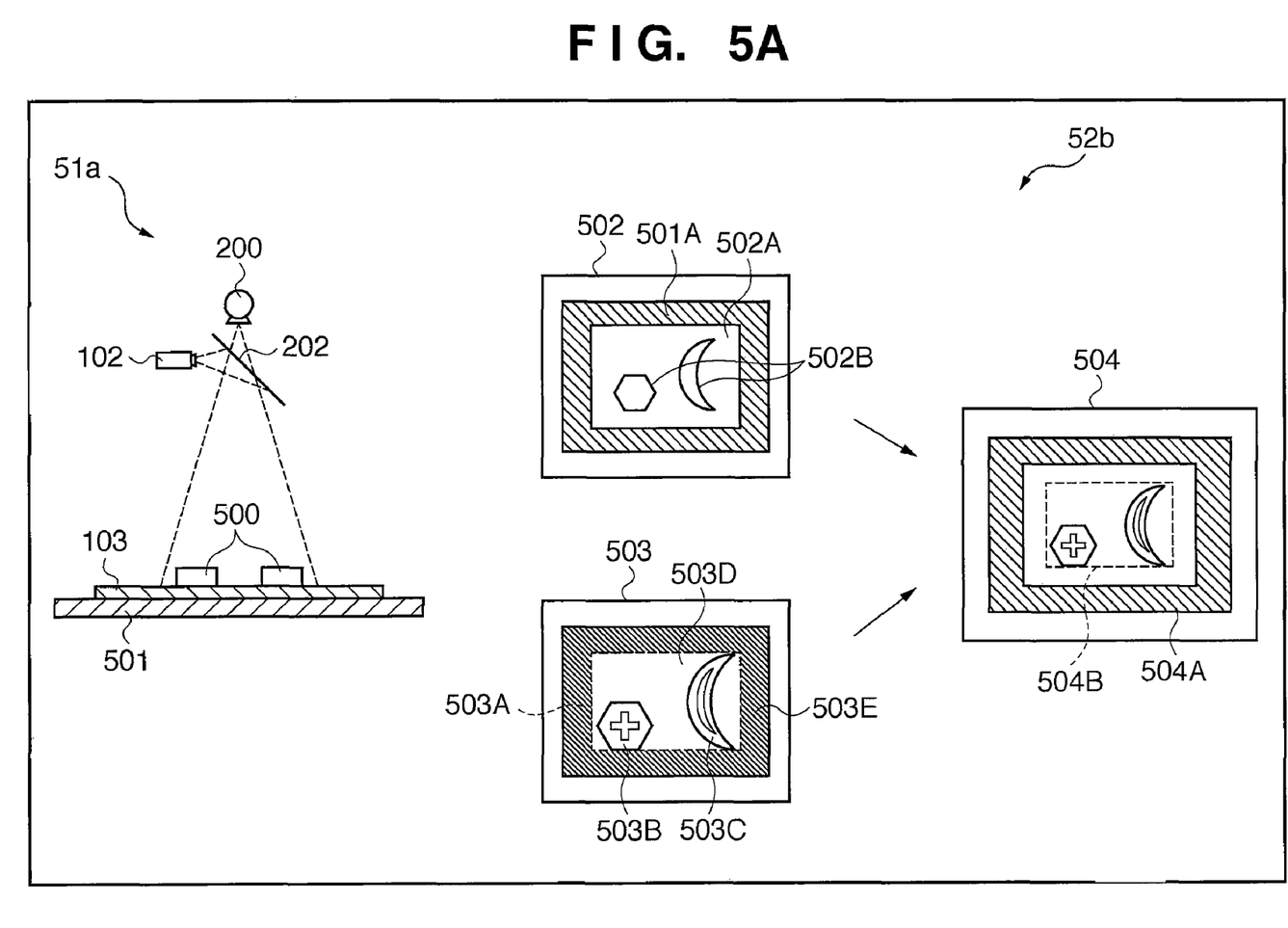
FIG. 5A is a view for explaining the registration of an irradiation field and the detection of a positional shift.

Referring to the view 51a in FIG. 5A, the X-rays irradiated from the X-ray tube 200 are transmitted through the object 500 and reach the X-ray sensor 103. The X-ray sensor 103 is placed on a bed 501. The TV camera 102 can capture a visual field region with the visible light reflected by the half mirror 202.

In the view 52b in FIG. 5A, reference numeral 502 denotes a visible picture captured by the TV camera 102. The visible picture 502 depicts a visible picture 501A of the bed 501, a visible picture 502A of the X-ray sensor 103, and a visible picture 502B of the object 500. These visible pictures (images) are acquire by the TV camera 102.

Reference numeral 503 denotes a radiograph acquired by the X-ray sensor 103. The radiograph 503 includes an image 503A showing an X-ray irradiated region (irradiation field region) and a partial image (a portion other than the irradiation field) 503E irradiated with no X-rays. In the view 52b in FIG. 5A, the image 503A showing the X-ray irradiated region (irradiation field region) includes partial images 503B and 503C corresponding to the detection of X-rays transmitted through the object 500, and a partial image 503D of a non-object region in which X-rays are directly detected.

A composite image 504 is generated by superimposing the visible picture 502 on the radiograph 503. In the composite image 504, reference numeral 504A denotes a display picture displayed on the display unit 105; and 504B, the irradiation field region of the radiograph. The irradiation field registration unit 307 specifies a specific portion of the visible image region captured by the TV camera 102 which becomes the irradiation field 503A of the radiograph 503. That is, the irradiation field registration unit 307 specifies the position information (position coordinates) of the irradiation field region of the radiograph included in the visible picture region, and stores the information in a memory such as the RAM (not shown).

Figure 5B:
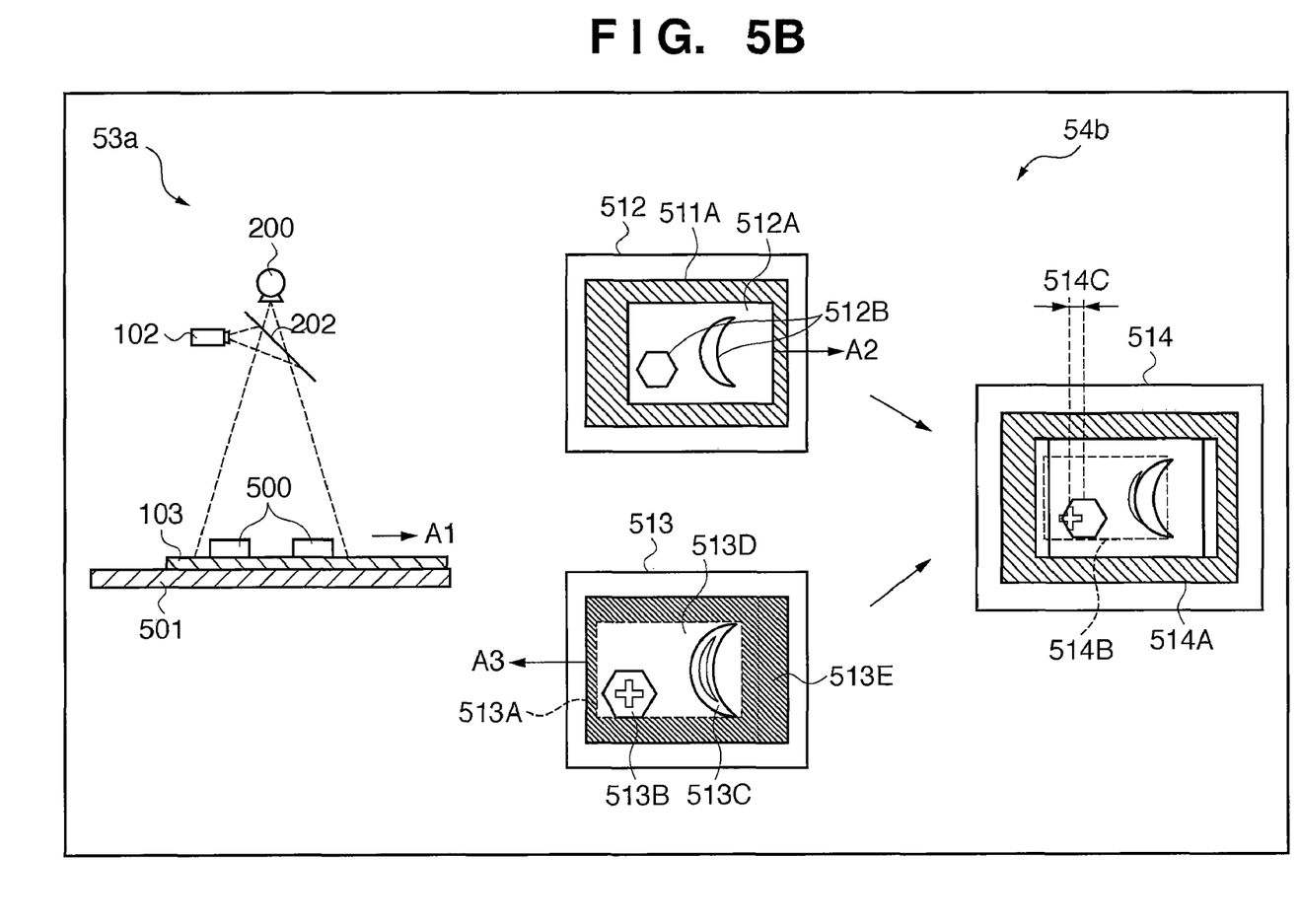
FIG. 5B is a view for explaining the registration of an irradiation field and the detection of a positional shift.

Reference numeral 53a in FIG. 5B denotes a view schematically showing a case in which the X-ray sensor 103 has moved in the direction of an arrow Al in the view 51a in FIG. 5A, and the relative positions of the X-ray tube 200 and the X-ray sensor 103 have changed.

In a view 54b in FIG. 5B, reference numeral 512 denotes a visible picture captured by the TV camera 102. The visible picture 512 depicts a visible picture 511A of the bed 501, a visible picture 512A of the X-ray sensor 103, and a visible picture 512B of the object 500. These visible pictures (images) are acquired by the TV camera 102.

When the X-ray sensor 103 moves in the direction of the arrow A1 in the view 53a in FIG. 5B, the visible picture 512A of the X-ray sensor 103 shifts from the visible picture 502A (52b in FIG. 5A) in the direction of an arrow A2.

Reference numeral 513 denotes a radiograph acquired by the X-ray sensor 103. The radiograph 513 includes an image 513A indicating an X-ray irradiated region (irradiation field region) and a partial image (a portion other than the irradiation field) 513E irradiated with no X-rays. In the view 54b in FIG. 5B, the image 513A showing the X-ray irradiated region (irradiation field region) includes partial images 513B and 513C corresponding to the detection of X-rays transmitted through the object 500, and a partial image 513D of a non-object region in which X-rays are directly detected. In the radiograph 513, the image 513A indicating the irradiation field region shifts from the image 503A indicating the X-ray irradiated region in the direction of an arrow A3 as the X-ray sensor 103 moves in the direction of the arrow A1.

A composite image 514 is generated by superimposing the visible picture 512 on the radiograph 513. In the composite image 514, reference numeral 514A denotes a display picture displayed on the display unit 105; and 514B, an image indicating the irradiation field region of the radiograph. The image 514B indicating the irradiation field region shifts from the image 504A indicating the irradiation field region shown in the view 52b in FIG. 5A to the left. Reference numeral 514C denotes a positional shift amount. The control unit 305 calculates the positional shift amount 514C based on the movement of the X-ray sensor 103. The image compositing unit 308 can perform display control on the display unit 105 in a state in which a shift from an irradiation field region registered in advance can be identified.

It is possible to detect the presence/absence of the relative positional shift between the X-ray tube 200 and the X-ray sensor 103 by registering in advance information indicating which part of a visible picture region corresponds to an X-ray irradiation field region and comparing the information with the position information registered during X-ray radioscopy.

The case in which the X-ray sensor 103 has moved has been described with reference to FIG. 5B. However, the above description applies to a case in which the X-ray tube 200 has moved or both the X-ray tube 200 and the X-ray sensor 103 have moved.

Note that in determination of whether there is a positional shift, an error may occur in, for example, determination on an X-ray irradiation field region. For this reason, it is preferable to set a threshold for determination of a positional shift amount and determine the occurrence of a positional shift when the positional shift amount exceeds the threshold.

As described above, according to this embodiment, it is possible to detect the presence/absence of a relative positional shift between the X-ray generation unit 101 and the X-ray sensor 103 during X-ray radioscopy and control X-ray irradiation based on the detection result.

Alternatively, if it is determined based on a detection result on the presence/absence of a positional shift that a positional shift has occurred, excessive irradiation and leakage of X-rays can be prevented by performing control to stop X-ray irradiation.

Alternatively, displaying guide information for guiding the user in operation to correct the relative positional shift between the X-ray generation unit 101 and the X-ray sensor 103 can implement an X-ray imaging apparatus with high convenience.

Second Embodiment

Figure 4:
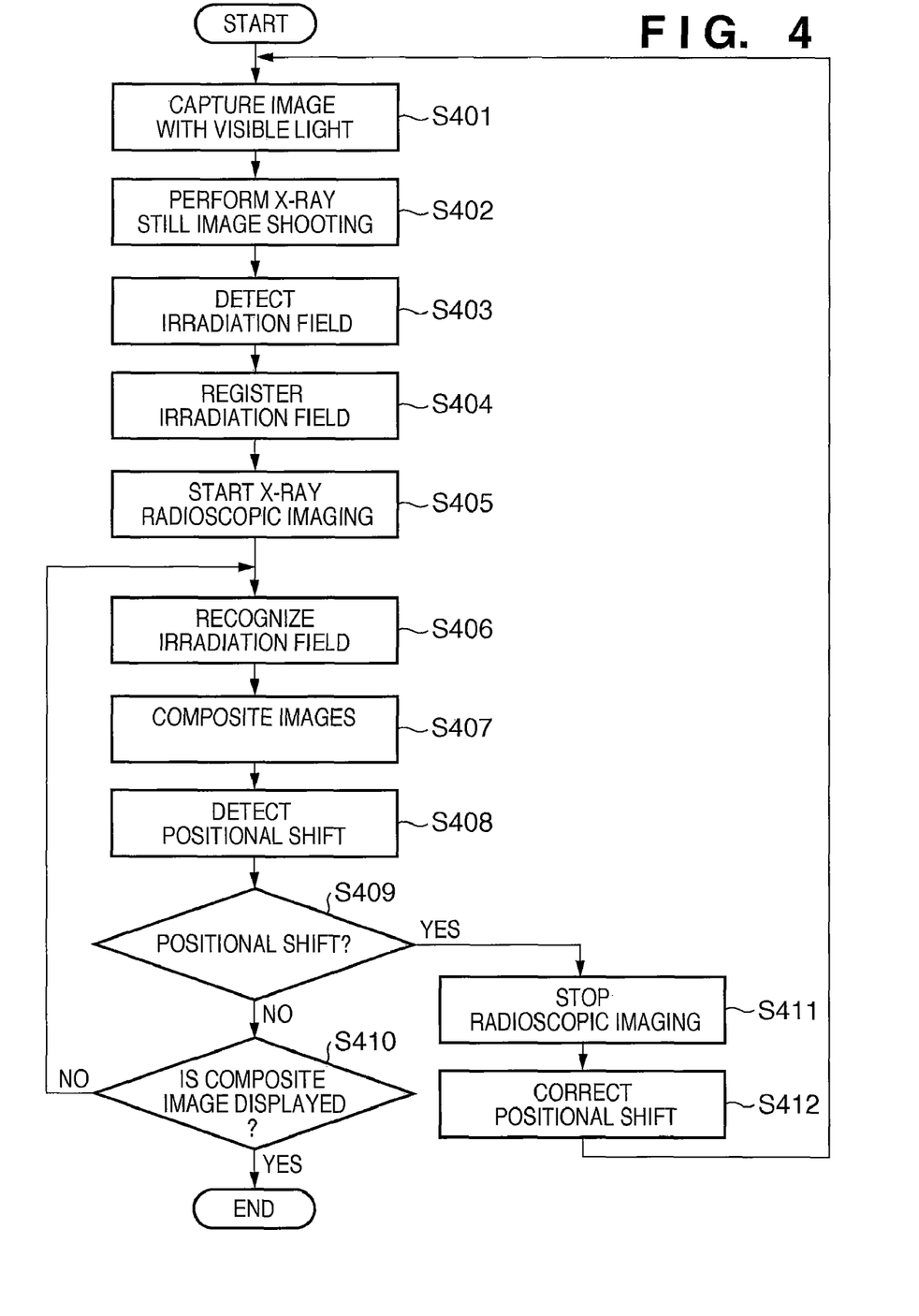
FIG. 4 is a flowchart for explaining a processing sequence at the time of X-ray imaging in the X-ray imaging apparatus according to the first embodiment.

The above description is about the arrangement in which the control unit 305 calculates a positional shift amount based on the detection result obtained by the shift detection unit 309, and the image compositing unit 308 displays guide information for correcting the positional shift amount on the display unit 105 in step S412 in FIG. 4 in the first embodiment. When a positional shift is detected, an image compositing unit 308 can also perform display control on a composite image, on a display unit 105, while switching transparencies for the superimposition of a visible picture and a radiograph in accordance with the calculated positional shift amount.

For example, holding the relationship between positional shift amounts and transparencies in a ROM in an X-ray imaging apparatus in the form of a lookup table allows an image compositing unit 308 to perform display control to change the transparency of either or both of a radiograph and a visible image in accordance with a calculated positional shift amount.

Switching the transparency of a composite image in accordance with a positional shift amount makes it possible to easily visually grasp the presence/absence of a relative positional shift between an X-ray generation unit 101 and an X-ray sensor 103.

The user can perform positioning (correction of a positional shift) between the X-ray generation unit 101 and the X-ray sensor 103 while recognizing a composite image on a display unit 105 with the transparent being switched. This arrangement can implement an X-ray imaging apparatus with high convenience.

Third Embodiment

Figure 6:
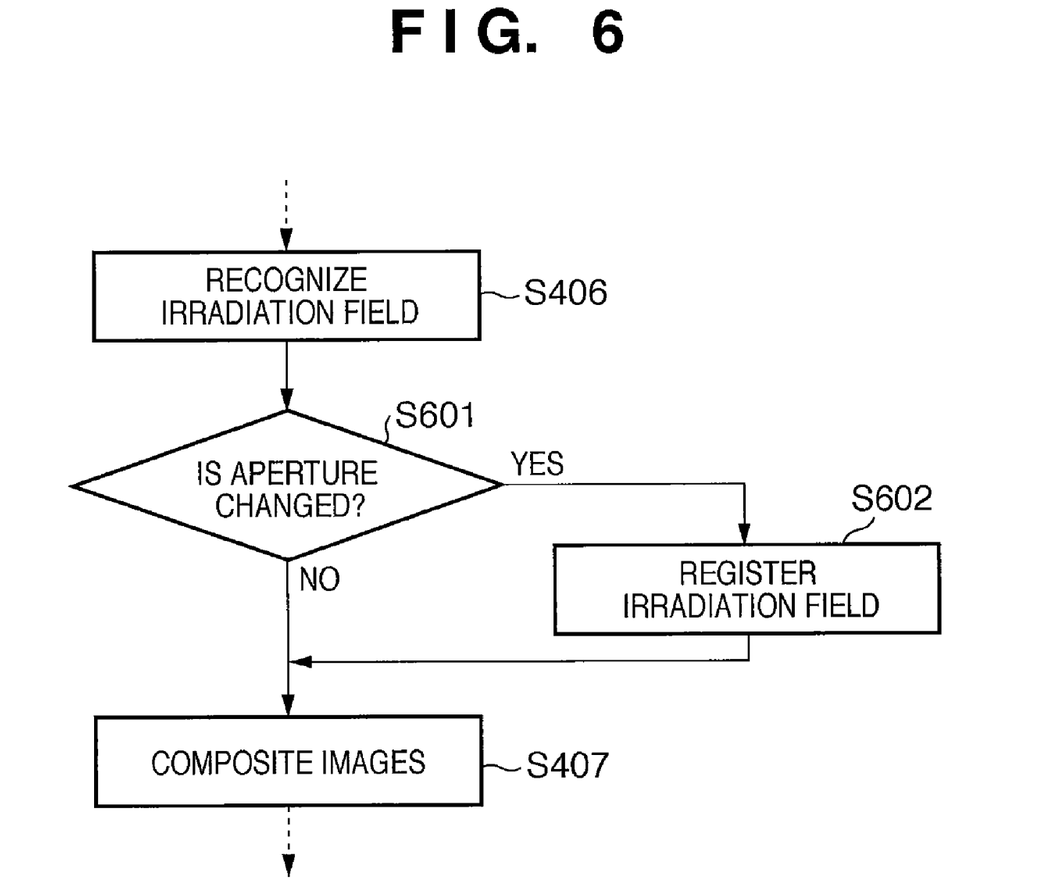
FIG. 6 is a flowchart for explaining a processing sequence at the time of X-ray imaging in an X-ray imaging apparatus according to the third embodiment.

The first embodiment has exemplified the arrangement configured to determine the presence/absence of a positional shift by detecting a change in the position information of an irradiation field region which is registered in advance. In this case, for example, even if there is no relative positional shift between an X-ray tube 200 and an X-ray sensor 103, when the aperture of a collimator 201 in an X-ray generation unit 101 changes, it is determined that a positional shift has occurred. The third embodiment exemplifies positional shift detection processing with high determination accuracy, which inhibits determination of the occurrence of a positional shift by registering an irradiation field again even when the aperture of the collimator 201 is changed. FIG. 6 is a flowchart for explaining a processing sequence in the third embodiment of the present invention. This processing is executed in steps S406 and S407 in FIG. 4 described in the first embodiment. The processing in steps S401 to S406 is the same as that in FIG. 4. In step S406, an irradiation field recognition unit 306 discriminates a region (irradiation field) irradiated with X-rays on the light-receiving surface of the X-ray sensor 103.

In step S601, a control unit 305 determines whether the aperture of the collimator 201 has been changed. The control unit 305 can determine, by monitoring a control signal to the collimator 201, whether the aperture of the collimator 201 has been changed. If the control unit 305 determines that the aperture of the collimator 201 has been changed (YES in step S601), the process advances to step S602. If the control unit 305 determines that the aperture of the collimator 201 has not been changed (NO in step S602), the process advances to step S407. Since the processing in step S407 and the subsequent steps is the same as that in FIG. 4, a description of the processing will be omitted to avoid redundancy.

In step S602, an irradiation field registration unit 307 registers the irradiated region (irradiation field) recognized in step S406 again. In this case, the information of the irradiation field after a change in aperture is overwritten on the information of the irradiated region (irradiation field) registered in step S404. The process then advances to step S407. With the above processing, the irradiated region (irradiation field) after the change in the aperture of the collimator 201 is registered in correspondence with the visible image acquired by the TV camera 102. In the processing in step S407 and the subsequent steps, the information of the irradiated region (irradiation field) registered again is used. Registering an irradiation field again and using the re-registration result for the determination of a positional shift can implement positional shift detection processing with high determination accuracy, which inhibits determination of the occurrence of a positional shift even when the aperture of the collimator 201 is changed.

Other Embodiments

The object of the present invention is implemented even by supplying a computer-readable storage medium storing software program codes for implementing the functions of the above embodiments to a system or apparatus, and causing the computer (or the CPU or MPU) of the system or apparatus to read out and execute the program codes stored in the storage medium.

In this case, the program codes read out from the storage medium implement the functions of the above embodiments by themselves, and the storage medium storing the program codes constitutes the present invention.

As a storage medium for supplying the program codes, for example, a flexible disk, hard disk, optical disk, magnetooptical disk, CD-ROM, CD-R, nonvolatile memory card, ROM, or the like can be used.

The functions of the above embodiments are implemented when the readout program codes are executed by the computer. Obviously, the functions of the above embodiments are also implemented when the OS (Operating System) running on the computer performs part or all of actual processing based on the instructions of the program codes.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2007-275670, filed Oct. 23, 2007, which is hereby incorporated by reference herein in its entirety.

What is claimed is:

1. An X-ray imaging apparatus comprising:
   a visible light imaging unit adapted to capture an image of a visual field region with visible light;
   an X-ray irradiation unit adapted to irradiate X-rays;
   an X-ray imaging unit adapted to receive X-rays irradiated by said X-ray irradiation unit and acquire a radiograph based on the X-rays;
   a detection unit adapted to detect a region irradiated with the X-rays on the basis of a radiograph acquired by said X-ray imaging unit;
   a registration unit adapted to register position information of the irradiated region of an image of the visual field region in a still image shooting mode;
   a detection unit adapted to detect the presence/absence of a relative positional shift between said X-ray irradiation unit and said X-ray imaging unit by comparing position information registered by said registration unit with position information based on an irradiated region of a radiograph acquired during movie shooting of performing X-ray imaging of an object; and an irradiation control unit adapted to control irradiation of the X-rays by said X-ray irradiation unit based on a detection result obtained by said positional shift detection unit.

2. The apparatus according to claim 1, further comprising an image compositing unit adapted to generate a composite image by superimposing an image of the visual field region on a radiograph acquired during capturing of the object,
wherein said image compositing unit displays the composite image on a display unit.

3. The apparatus according to claim 2, wherein
said irradiation control unit calculates a positional shift amount based on a detection result obtained by said positional shift detection unit, and
said image compositing unit generates the composite image by switching transparency of one of an image of the visual field region and a radiograph acquired during capturing of the object in accordance with the positional shift amount.

4. The apparatus according to claim 2, wherein said image compositing unit displays, in the composite image, guide information for guiding positioning operation for one of said X-ray irradiation unit and said X-ray imaging unit to correct the positional shift.

5. The apparatus according to claim 1, further comprising
a changing unit adapted to change an aperture for X-rays irradiated from said X-ray irradiation unit, and
a determination unit adapted to determine whether the aperture is changed by said changing unit,
wherein when a determination result obtained by said determination unit indicates that the aperture is changed, said registration unit registers position information of an X-ray irradiated region based on the changed aperture.

6. The apparatus according to claim 5, wherein said positional shift detection unit detects the presence/absence of a relative positional shift between said X-ray irradiation unit and said X-ray imaging unit by comparing position information of the X-ray irradiated region registered again with position information based on an irradiated region of a radiograph acquired during capturing of an object.

7. A control method for an X-ray imaging apparatus, the method comprising:
a visible light capturing step of causing a visible light imaging unit to capture an image of a visual field region with visible light;
an X-ray irradiation step of causing an X-ray irradiation unit to irradiate X-rays;
an x-ray image capturing step of causing an X-ray imaging unit to receive X-rays irradiated in the X-ray irradiation step and acquire a radiograph based on the X-rays;
a detection step of causing a detection unit to detect an irradiated region irradiated with the X-rays based on a radiograph acquired in the X-ray image capturing step;
a registration step of causing a registration unit to register position information of the irradiated region of an image of the visual field region in a still image shooting mode;
a positional shift detection step of causing a positional shift detection unit to detect the presence/absence of a relative positional shift between the X-ray irradiation unit and the X-ray imaging unit by comparing position information registered in the registration step with position information based on an irradiated region of a radiograph acquired during movie shooting of performing X-ray imaging of an object; and
an irradiation control step of causing an irradiation control unit to control irradiation of the X-rays in the step of irradiating X-rays on the basis of a detection result obtained in the positional shift detection step.

8. The method according to claim 7, further comprising an image compositing step causing an image compositing unit to generate a composite image by superimposing an image of the visual field region on a radiograph acquired during capturing of the object,
wherein in the step of combining images, the composite image is displayed on a display unit.

9. The method according to claim 8, wherein
in the irradiation control step, a positional shift amount is calculated based on a detection result obtained by the positional shift detection unit, and
in the image compositing step, the composite image is generated by switching transparency of one of an image of the visual field region and a radiograph acquired during capturing of the object in accordance with the positional shift amount.

10. The method according to claim 8, wherein in the image compositing step, guide information for guiding positioning operation for one of the X-ray irradiation unit and the X-ray imaging unit is displayed in the composite image to correct the positional shift.

11. The method according to claim 7, further comprising
a changing step of causing a changing unit to change an aperture for X-rays irradiated from the X-ray irradiation unit, and
a determination step of causing a determination unit to determine whether the aperture is changed in the changing step,
wherein when a determination result obtained in the determination step indicates that the aperture is changed, position information of an X-ray irradiated region based on the changed aperture is registered again in the registration step.

12. The method according to claim 11, wherein in the positional shift detection step, the presence/absence of a relative positional shift between the X-ray irradiation unit and the X-ray imaging unit is detected by comparing position information of the X-ray irradiated region registered again with position information based on an irradiated region of a radiograph acquired during capturing of an object.

13. A program which is stored in a computer-readable storage medium and causes a computer to execute a control method for an X-ray imaging apparatus defined in claim 7.

14. A computer-readable storage medium which stores a program defined in claim 13.

* * * * *